(12) United States Patent
Munetou et al.

(10) Patent No.: US 6,680,405 B1
(45) Date of Patent: Jan. 20, 2004

(54) PROCESS FOR THE PREPARATION OF METHYL METHACRYLATE

(75) Inventors: Akio Munetou, Otake (JP); Hideyasu Takezawa, Otake (JP); Shuhei Otsuka, Otake (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 10/048,465

(22) PCT Filed: Aug. 6, 1999

(86) PCT No.: PCT/JP99/04268

§ 371 (c)(1),
(2), (4) Date: Feb. 6, 2002

(87) PCT Pub. No.: WO01/10811

PCT Pub. Date: Feb. 15, 2001

(51) Int. Cl.$^7$ ................................................. C07C 69/52
(52) U.S. Cl. ....................................... 560/205; 560/129
(58) Field of Search ............................ 560/1, 205, 208, 560/209

(56) References Cited

FOREIGN PATENT DOCUMENTS

| JP | 57-9739 | 1/1982 |
|----|---------|--------|
| JP | 57-9740 | 1/1982 |
| JP | 58-157740 | 9/1983 |
| JP | 58-180457 | 10/1983 |
| JP | 7-69948 | 3/1995 |
| JP | 8-268938 | 10/1996 |
| JP | 10-306052 | 11/1998 |
| JP | 11-228498 | 8/1999 |

Primary Examiner—Johann Richter
Assistant Examiner—Karl J. Puttlitz
(74) Attorney, Agent, or Firm—Oblon, Spivak, McClelland, Maier & Neustadt, P.C.

(57) ABSTRACT

A process for producing methyl methacrylate, which comprises subjecting methacrolein and methanol to direct esterification reaction to thereby obtain a reaction mixture liquid containing at least methyl methacrylate and methanol, adding additional methacrolein to the reaction mixture liquid as an entrainer, and distilling the resulting reaction mixture liquid to recover the methanol.

20 Claims, No Drawings

PROCESS FOR THE PREPARATION OF METHYL METHACRYLATE

The present invention relates to a process for producing methyl methacrylate, according to which methanol can be recovered by distillation from a reaction mixture liquid, which is obtained by direct esterification reaction between methacrolein and methanol and which contains at least methyl methacrylate and methanol, and the recovered methanol can be used as a material for the direct esterification reaction.

BACKGROUND ART

For recovering methanol by distillation from a reaction mixture liquid containing methyl methacrylate and methanol, JP-B-1-47454 proposes a process comprising feeding a saturated hydrocarbon having 6 to 8 carbon atoms to a distillation column, thereby separating methanol and the like.

As a similar process, JP-A-57-9740 proposes a process, in which at the time when methyl methacrylate is refined by distillation in a manner such that a mixture liquid containing methanol, water and methyl methacrylate is fed to a distillation column, a saturated hydrocarbon having 6 to 7 carbon atoms is placed at a plate(s) substantially above a plate to which the foregoing mixture liquid is fed, and as a result, the saturated hydrocarbon and substantially whole amount of methanol are distilled out from a top of the column and are subjected to separation through a phase separation tank, and thereafter the methanol phase is supplied to a second distillation column to recover methanol from a bottom of the column.

Further, JP-A-58-180457 discloses that methanol can be separated in a manner such that an entrainer capable of forming an azeotrope with methanol in the presence of methyl methacrylate and water is added to a mixture containing methanol, water and methyl methacrylate, followed by azeotropic distillation, thereby a mixture of the entrainer and methanol is obtained from a top of the column, and, when the mixture forms two phase, these two phases are separated from each other. In said JP-A, in addition to hydrocarbon solvents such as n-hexane, n-octane, cyclohexane, benzol and toluol, solvents such as diisopropyl ether, tetrahydrofuran and dimethyl carbonate are exemplified as suitable entrainer.

Furthermore, JP-A-7-69948 discloses that methanol is recovered in a manner such that a hydrocarbon solvent and water are added to a reaction mixture liquid to obtain a blend liquid, the blend liquid is separated into two phases of an organic phase and a hydrous methanol phase, and then methanol is separated by distillation from the hydrous methanol phase.

However, according to these processes, in distilling, a large amount of the hydrocarbon is added as the entrainer to carry out the azeotropic distillation, and as a result, the distillation needs a great deal of utilities. Moreover, when attempting to produce methyl methacrylate by using the recovered methanol for direct esterification reaction with methacrolein, it is necessary to separate the entrainer contained in the recovered methanol by means of distillation, extraction or the like, so that the procedure becomes troublesome.

Besides the foregoing processes, there are processes for recovering methanol by distillation of the reaction mixture liquid without use of any entrainer. However, according to such processes, the recovered methanol contains a large amount of the object product of the direct esterification reaction, namely methyl methacrylate, and therefore such processes are not efficient.

DISCLOSURE OF INVENTION

Accordingly, an object of the present invention is to provide a process for producing methyl methacrylate, according to which methanol can be recovered by distillation from a reaction mixture liquid, which is obtained by direct esterification reaction between methacrolein and methanol and which contains at least methyl methacrylate and methanol, and the recovered methanol is used as a material for the direct esterification reaction, wherein any hydrocarbon, which should be separated and removed later, is not used as the entrainer for simplifying the procedures when recovering the methanol by distillation, and thereby a content of methyl methacrylate in the recovered methanol can be reduced.

The present inventors have undertaken extensive studies, and as a result, it has been found that the above-mentioned problems can be solved by adding additional methacrolein as an entrainer when recovering methanol by distillation. Thereby, the present invention has been accomplished.

That is, the present invention provides a process for producing methyl methacrylate, which comprises subjecting methacrolein and methanol to direct esterification reaction to thereby obtain a reaction mixture liquid containing at least methyl methacrylate and methanol, adding additional methacrolein to said reaction mixture liquid as an entrainer, and distilling the resulting reaction mixture liquid to recover the methanol.

In the present invention, the recovered methanol can be used as a material for the production of methyl methacrylate by the direct esterification reaction.

BEST MODE FOR CARRYING OUT THE INVENTION

In the present invention, a process for producing methyl methacrylate by direct esterification reaction between methacrolein and methanol, hereinafter referred to as "direct esterification reaction" for brevity, is not particularly limited, and may be any of a gas phase or liquid phase reaction. How to carry out the reaction is also not particularly limited, and the reaction may be carried out in any of a continuous or batch manner. For example, there can be given a process comprising carrying out the reaction using a palladium based catalyst in a liquid phase in a continuous manner.

Although the reaction mixture liquid obtained by the direct esterification reaction usually contains a non-reacted material and a product of methyl methacrylate, a reaction mixture liquid pertaining to the present invention is that containing at least a non-reacted material of methanol and a product of methyl methacrylate.

The methanol and methyl methacrylate concentrations in the reaction mixture liquid vary depending upon the reaction conditions and the like. For example, when the reaction is carried out in a liquid phase using a palladium based catalyst, the methanol concentration in the reaction mixture liquid is usually from 25 to 70% by weight, and the methyl methacrylate concentration therein is usually from 20 to 60% by weight. Besides these, the reaction mixture liquid usually contains a non-reacted material of methacrolein, a by-product of methyl formate, water and others.

When it is required to remove low boiling by-products such as methyl formate from the reaction mixture liquid, it is permitted to add an operation before the distillation for the recovery of methanol, which operation is carried out, for example, in a manner such that the reaction mixture liquid is fed in advance to a distillation column and the low boiling by-products are distillation-removed with a part of methacrolein and methanol from a top of the column.

In the present invention, in recovering methanol from the reaction mixture liquid by distillation, additional methacrolein is added to the reaction mixture liquid as an entrainer. A process for adding the additional methacrolein thereto is not particularly limited. For example, there are given a process comprising feeding the reaction mixture liquid and the methacrolein to suitable positions of the distillation column, respectively, and a process comprising adding the methacrolein to the reaction mixture liquid, followed by feeding to the distillation column. By the distillation, methanol can be taken out from a top of the column together with methacrolein which has azeotropic point with methanol.

An addition amount of the additional methacrolein used for such a purpose is preferably from 20 to 200 parts by weight, particularly preferably from 40 to 80 parts by weight based on 100 parts by weight of the methanol contained in the reaction mixture liquid. When the amount of the methacrolein is less than 20 parts by weight, methyl methacrylate may be distilled out in a large amount at the time of recovering methanol, thereby making the recovery of methanol difficult. When it exceeds 200 parts by weight, an excess amount of the methacrolein is recycled to a reactor, and as a result, the reaction may be adversely effected in a manner such that it becomes difficult to control a ratio of the materials of methanol and methacrolein within a suitable range, or methacrolein may be polymerized by itself.

In the present invention, a form of the distillation column used for the recovery of methanol is not particularly limited, and may be a conventional one such as a plate type and a packed type. When the liquid in the column forms two phases, water may be separated and taken out with use of a decanter. Although the distillation conditions are not particularly limited, it is preferred to apply normal pressure or reduced pressure as distillation pressure and a temperature of not higher than 120° C. as a column bottom temperature to inhibit any polymerization.

In the present invention, the methanol recovered by distillation contains methacrolein. Methanol and methacrolein concentrations in the recovered methanol vary depending upon the reaction mixture liquid to be distilled, operation conditions of the distillation and the like. The methanol concentration is usually from 30 to 70% by weight and the methacrolein concentration is usually from 20 to 70% by weight.

The thus recovered methanol can be used as a material for the production of methyl methacrylate by direct esterification reaction as it is. In using it as a material for the production of methyl methacrylate by direct esterification reaction in the original reactor or another reactor, usually methanol and methacrolein are suitably added to adjust to desired material concentrations or desired amounts to be fed.

The present invention is explained with reference to Example and Comparative Example as follows. The weight compositions of the reaction mixture liquid and the like were analyzed by means of gas-chromatography.

EXAMPLE 1

In a 4 liter reactor equipped with a condenser and a stirrer, 350 g of a catalyst (a calcium carbonate catalyst containing 5% by weight palladium-1% by weight lead-1% by weight iron) and a reaction liquid of 700 g of methacrolein and 1280 g of methanol were charged, and the reaction was continued for 4 hours at a bath temperature of 80° C. under pressure of 400 kPa·abs, while blowing air and nitrogen at rates of 4.77 Nl/min and 5.0 Nl/min, respectively, thereby to synthesize methyl methacrylate. The reaction product was collected and analyzed, and as a result, a conversion of methacrolein and a selectivity of methyl methacrylate were found to be 75.1% and 85.2%, respectively.

The thus obtained reaction mixture liquid collected was fed to a distillation column having 50 plates, and low boiling materials such as methyl formate were distilled out from a top of the column. The reaction mixture liquid, after such distillation, was found to have a composition comprising 32.1% by weight of methyl methacrylate, 51.1% by weight of methanol, 8.8% by weight of methacrolein and 6.4% by weight of water.

Successively, distillation was carried out at a reflux ratio of 2.0 under column top pressure of 80 kPa·abs, while feeding said liquid to the 25th plate of Oldershaw type distillation column having 50 plates at 394.7 g/h and feeding methacrolein to the 24th plate thereof at 105.3 g/h. As a result, from a top of the distillation column, a distillate containing 53.9% by weight of methanol, 37.4% by weight of methacrolein and 7.4% by weight of methyl methacrylate was obtained at 374.1 g/h, and from a bottom of the column, a liquid containing 78.8% by weight of methyl methacrylate and 16.4% by weight of water, in other words, containing substantially neither methacrolein nor methanol, was obtained at 125.8 g/h. A partition ratio of methyl methacrylate in the distillate to that of the column bottom liquid was found to be 0.28. Although the distillate obtained from the column top contains a small amount of methyl methacrylate, the distillate could be used without any problem as a material for the direct esterification reaction by supplying methanol and methacrolein.

COMPARATIVE EXAMPLE 1

Distillation was carried out to recover methanol in the same manner as in Example 1 except that no methacrolein was fed to the distillation column. As a result, from a top of the distillation column, a liquid containing 72.0% by weight of methanol, 12.3% by weight of methacrolein and 14.7% by weight of methyl methacrylate was obtained at 280.0 g/h, and from a bottom of the column, a liquid containing 74.7% by weight of methyl methacrylate and 20.1% by weight of water, in other words containing substantially neither methacrolein nor methanol, was obtained at 114.7 g/h. However, a partition ratio of methyl methacrylate in the distillate to that of the column bottom liquid was found to be 0.48, which was larger than that in Example 1.

INDUSTRIAL APPLICABILITY

According to the present invention, methanol can be recovered by distillation from a reaction mixture liquid, which is obtained by direct esterification reaction between methacrolein and methanol and which contains at least methyl methacrylate and methanol, the procedure can be simplified when the recovered methanol is used as a material for the direct esterification reaction, and a content of methyl methacrylate in the recovered methanol can be reduced, so that the object product of methyl methacrylate can be efficiently produced.

What is claimed is:

1. A process for producing methyl methacrylate, comprising esterifying a mixture comprising methacrolein and methanol to form a reaction mixture liquid comprising at least methyl methacrylate and methanol, adding additional methacrolein to said reaction mixture liquid, and distilling the reaction mixture liquid to recover the methanol.

2. The process according to claim 1, further comprising esterifying a mixture of the recovered methanol and methacrolein.

3. The process according to claim 1, wherein the additional methacrolein is added to the reaction mixture liquid during distilling.

4. The process according to claim 3, wherein the additional methacrolein is added in a distillation column.

5. The process according to claim 1, wherein the additional methacrolein is added to the reaction mixture liquid before distilling.

6. The process according to claim 1, further comprising distilling low boiling materials from the reaction mixture liquid before adding additional methacrolein.

7. The process according to claim 1, wherein esterifying includes contacting the methacrolein and methanol in the presence of a catalyst.

8. The process according to claim 1, wherein the recovered methanol comprises methacrolein.

9. The process according to claim 7, wherein the recovered methanol further comprises methyl methacrylate.

10. The process according to claim 1, further comprising isolating an azeotrope of methanol and methacrolein.

11. The process according to claim 1, wherein the reaction mixture liquid comprises from 25 to 70% by weight of methanol and from 20 to 60% by weight of methylmethacrylate.

12. The process according to claim 1, wherein the amount of additional methacrolein added to the reaction mixture liquid is from 20 to 200 parts by weight, based on 100 parts by weight of the methanol in the reaction mixture liquid.

13. The process according to claim 1, wherein the amount of the additional methacrolein added to the reaction mixture liquid is from 40 to 80 parts by weight based on 100 parts by weight of the methanol in the reaction mixture liquid.

14. The process according to claim 1, further comprising separating water with a decanter during distilling.

15. The process according to claim 1, wherein the temperature of the reaction mixture liquid is not higher than 120° C. during distilling.

16. A process for producing methyl methacrylate, comprising esterifying a mixture comprising methacrolein and methanol to form a reaction mixture liquid comprising at least methyl methacrylate and methanol, adding additional methacrolein to said reaction mixture liquid, and distilling the reaction mixture liquid to recover the methanol.

wherein the methacrolein is added to the reaction mixture liquid during distilling in a distillation column.

17. The process according to claim 16, wherein the reaction mixture liquid comprises from 25 to 70% by weight of methanol and from 20 to 60% by weight of methylmethacrylate.

18. The process according to claim 16, wherein the amount of additional methacrolein added to the reaction mixture liquid is from 20 to 200 parts by weight based on 100 parts by weight of the methanol in the reaction mixture liquid.

19. The process according to claim 16, wherein the amount of additional methacrolein added to the reaction mixture liquid is from 40 to 80 parts by weight based on 100 parts by weight of the methanol in the reaction mixture liquid.

20. The process according to claim 16, wherein the temperature of the reaction mixture liquid is not higher than 120° C. during distilling.

* * * * *